(12) United States Patent
Sarpotdar et al.

(10) Patent No.: US 9,925,194 B2
(45) Date of Patent: Mar. 27, 2018

(54) KINETIN/ZEATIN TOPICAL FORMULATION

(71) Applicant: Dow Pharmaceutical Sciences, Inc., Petaluma, CA (US)

(72) Inventors: Pramod P. Sarpotdar, Irvine, CA (US); Sarmistha Basu, Santa Rosa, CA (US); Varsha D. Bhatt, San Francisco, CA (US); Yunik Chang, Clermont, FL (US); Gordon J. Dow, Santa Rosa, CA (US)

(73) Assignee: Dow Pharmaceutical Sciences, Inc., Petaluma, CA (US)

( * ) Notice: Subject to any disclaimer, the term of this patent is extended or adjusted under 35 U.S.C. 154(b) by 0 days.

(21) Appl. No.: 15/483,898

(22) Filed: Apr. 10, 2017

(65) Prior Publication Data

US 2017/0209453 A1    Jul. 27, 2017

Related U.S. Application Data

(63) Continuation of application No. 14/216,722, filed on Mar. 17, 2014, now Pat. No. 9,616,132.

(60) Provisional application No. 61/798,656, filed on Mar. 15, 2013.

(51) Int. Cl.
| | |
|---|---|
| *A61K 31/52* | (2006.01) |
| *A61K 9/127* | (2006.01) |
| *A61K 47/10* | (2017.01) |
| *A61K 47/12* | (2006.01) |
| *A61K 9/00* | (2006.01) |
| *A61K 9/06* | (2006.01) |
| *A61Q 19/00* | (2006.01) |
| *A61K 8/14* | (2006.01) |
| *A61K 8/49* | (2006.01) |
| *A61K 8/86* | (2006.01) |
| *A61K 8/36* | (2006.01) |

(52) U.S. Cl.
CPC .............. *A61K 31/52* (2013.01); *A61K 8/14* (2013.01); *A61K 8/361* (2013.01); *A61K 8/4953* (2013.01); *A61K 8/86* (2013.01); *A61K 9/0014* (2013.01); *A61K 9/06* (2013.01); *A61K 9/127* (2013.01); *A61K 47/10* (2013.01); *A61K 47/12* (2013.01); *A61Q 19/00* (2013.01); *A61K 2800/524* (2013.01)

(58) Field of Classification Search
CPC .......... A61K 8/498; A61K 8/97; A61K 8/347; A61K 8/37; A61K 8/64; A61K 2800/412; A61K 8/42; A61K 8/602; A61K 31/137; A61K 31/203; A61K 31/4436; A61K 8/67
See application file for complete search history.

(56) References Cited

U.S. PATENT DOCUMENTS

| | | | |
|---|---|---|---|
| 6,610,322 B1 | 8/2003 | Keller | |
| 7,785,623 B2 * | 8/2010 | Keller ...................... | A61K 8/14 424/401 |
| 2008/0076720 A1 * | 3/2008 | Xie ........................ | A61K 8/368 514/18.8 |

FOREIGN PATENT DOCUMENTS

JP    2009263346 A  *  11/2009  ............... A61K 8/49

OTHER PUBLICATIONS

Chessa, M. et al., "Effect of penetration enhancer containing vesicles on the percutaneous delivery of quercetin through new born pig skin," Pharmaceutics, 3(3):497-509, 2011.

* cited by examiner

*Primary Examiner* — Nannette Holloman
(74) *Attorney, Agent, or Firm* — Kilpatrick Townsend & Stockton LLP

(57) ABSTRACT

The solubility of kinetin and/or of zeatin is increased when either or both are combined in a formulation that includes a polyoxyalkylene-n-glycerol dicarboxylate component and a fatty acid component. These two components provide a synergistic increase in the solubility of kinetin and/or zeatin that is greater than that which would be expected based on the solubility of kinetin and zeatin in the individual components.

18 Claims, No Drawings

KINETIN/ZEATIN TOPICAL FORMULATION

CROSS-REFERENCES TO RELATED APPLICATIONS

This application is a continuation of U.S. patent application Ser. No. 14/216,722, filed Mar. 17, 2014, which claims priority from U.S. Patent Application No. 61/798,656, filed Mar. 15, 2013, and entitled "Kinetin/Zeatin Topical Formulation," the disclosure of which is incorporated by reference herein for all purposes.

FIELD OF THE INVENTION

This application pertains to the field of topical pharmacological compositions, particularly those containing either or both of kinetin and zeatin.

BACKGROUND OF THE INVENTION

Kinetin ($N^6$-furfuryladenine) (CAS #525-79-1) is a derivative of adenine which is one of the nucleic acid purine bases, and it belongs to the cytokinin group of plant growth hormones. Kinetin is an amphoteric compound which is soluble in strong acids, alkalis, and glacial acetic acid, is slightly soluble in ethanol, butanol, acetone and ether, but is practically insoluble in distilled water. Although the exact mechanisms of action of kinetin are yet to be revealed, various lines of evidence indicate that kinetin is involved in signal transduction and also acts as a natural antioxidant. Since 1994, kinetin has been thoroughly tested for its powerful anti-aging effects in human skin cells and other systems.

Zeatin ((E)-2-methyl-4-(7H-purin-6-ylamino)but-2-en-1-ol) (CAS #1637-39-4), a plant hormone and derivative of adenine, was originally purified from immature kernels of the corn *Zea mays*, and was later identified to be present in the tRNA of a wide variety of organisms. It has been known to promote maintenance of small cell size (a key determinant of youthful skin) and structural and functional integrity of cells. Zeatin exists in two forms, trans and cis. The activity of zeatin is attributed to its more stable trans form.

At present, kinetin and zeatin are widely used components in numerous skin care cosmetic therapies, such as Kinerase® and ProTherapy MD® (Valeant Pharmaceuticals International Inc., Bridgewater, N.J.). Kinetin and zeatin each has been used in cosmetic formulations at concentrations up to 0.2% for kinetin and up to 0.1% for zeatin. Kinetin and zeatin, in addition to being practically insoluble in water, are very difficult to solubilize in solvents suitable for use in cosmetic formulations at meaningful concentrations. Unfortunately, extensive evaluations have failed to identify a cosmetic ingredient with good solubilizing capacity for kinetin, zeatin, or both in combination Hydrophilic penetration enhancing agents that improve the solubility of a drug in water, such as Transcutol® (Gattefosse, St. Priest, France), propylene glycol, polyethylene glycol, and Labrasol® (Gattefosse), have been used to increase the penetration of a drug that is solubilized within a liposome. As reported in Chessa et al., *Pharmaceutics*, 3:497-509 (2011), the inclusion of such hydrophilic agents in a formulation in which the drug is solubilized within a liposome has no deleterious effect on the solubility of the drug in the formulation with the addition of water.

The effectiveness of topical pharmaceutical agents such as kinetin and zeatin can be enhanced when the amount of the agent that is dissolved, relative to the amount that is in suspension, in a formulation is increased. Moreover, the effectiveness of topical cosmetic and pharmaceutical agents is generally enhanced by the use of agents that increase penetration of the agents into skin. Water is a desirable vehicle for topical formulations because, unlike organic solvents, water does not dry the skin or irritate damaged skin. However, because water is a poor solvent for kinetin and zeatin, a significant need exists for a solution to the problem of increasing the solubility of kinetin and/or zeatin in pharmaceutical formulations that contain water as a major ingredient.

SUMMARY OF THE INVENTION

It has surprisingly been found that the solubility of kinetin and/or of zeatin is increased when either or both are combined in a formulation that includes a polyoxyalkylene-n-glycerol dicarboxylate component and a fatty acid component. These two components provide a synergistic increase in the solubility of kinetin and/or zeatin that is greater than that which would be expected based on the solubility of kinetin and zeatin in the individual components.

As such, in one embodiment, the present invention provides a method for increasing the solubility of kinetin and/or zeatin comprising combining the kinetin and/or zeatin in a formulation comprising: a polyoxyalkylene-n-glycerol dicarboxylate and a fatty acid, wherein the amounts of the polyoxyalkylene-n-glycerol dicarboxylate and the fatty acid are sufficient to provide a synergistic increase in the solubility of the kinetin and/or the zeatin in the formulation.

As disclosed herein, the polyoxyalkylene-n-glycerol dicarboxylate includes a polyoxyalkylene component and an n-glycerol dicarboxylate component. In one embodiment, the polyoxyalkylene component includes, but is not limited to, paraformaldehyde, polyethylene glycol, polypropylene glycol, and polytetramethylene glycol. In another embodiment, the n-glycerol dicaroboylate component includes, but is not limited to, glyceryl dilaurate, glyceryl diarachidate, glyceryl dibehenate, glyceryl dierucate, glyceryl dihydroxystearate, glyceryl diisopalmitate, glyceryl diisostearate, glyceryl dilinoleate, glyceryl dimyristate, glyceryl dioleate, glyceryl diricinoleate, glyceryl dipalmitate, glyceryl dipalmitoleate, glyceryl distearate, glyceryl palmitate lactate, glyceryl stearate citrate, glyceryl stearate lactate, and glyceryl stearate succinate. In another embodiment, the polyoxyalkylene component includes, but is not limited to, paraformaldehyde, polyethylene glycol, polypropylene glycol, and polytetramethylene glycol, and the n-glycerol dicaroboylate component includes, but is not limited to, glyceryl dilaurate, glyceryl diarachidate, glyceryl dibehenate, glyceryl dierucate, glyceryl dihydroxystearate, glyceryl diisopalmitate, glyceryl diisostearate, glyceryl dilinoleate, glyceryl dimyristate, glyceryl dioleate, glyceryl diricinoleate, glyceryl dipalmitate, glyceryl dipalmitoleate, glyceryl distearate, glyceryl palmitate lactate, glyceryl stearate citrate, glyceryl stearate lactate, and glyceryl stearate succinate.

In addition to the the polyoxyalkylene-n-glycerol dicarboxylate, the kinetin and/or zeatin is combined with a fatty acid component. The fatty acid component is one or more fatty acids that are liquid at room temperature and/or that have a branched or unbranched chain of 12 to 20 carbons. In one embodiment, the fatty acid component is a mixture of branched and straight chain unsaturated C18 fatty acids. In another embodiment, the fatty acid component is a mixture of fatty acids having between 12 and 20 carbons and the fatty acids can be saturated or unsaturated. In yet another embodiment, the fatty acid component comprises a mixture of fatty acids. The mixture of fatty acids can include branched and straight chain fatty acids, especially those having from about 12 to about 20 carbons. Moreover, the mixture of fatty acids can comprise saturated and unsaturated fatty acids.

In certain embodiments, the polyoxyalkylene-n-glycerol dicarboxylate component is PEG-12 Glycerol dimyristate or PEG-12 Glycerol dioleate. In certain embodiments, the fatty acid is isostearic acid. As such, in one embodiment, the polyoxyalkylene-n-glycerol dicarboxylate component is PEG-12 Glycerol dimyristate and the fatty acid is isosteatic acid. In another embodiment, the polyoxyalkylene-n-glycerol dicarboxylate component is PEG-12 Glycerol dioleate and the fatty acid is isosteatic acid.

In another aspect, the present invention provides a formulation comprising: kinetin and/or zeatin in which the kinetin and/or zeatin is contained as part of a liposome and wherein the kinetin and zeatin do not precipitate from the formulation in the presence of water. In one embodiment, the formulation comprises a liposome forming agent and a lipophilic skin penetration enhancing agent.

In still another embodiment, the present invention provides a formulation comprising kinetin and/or zeatin, a liposome forming agent and a lipophilic skin penetration enhancing agent. As set forth in the Examples provided herein, it has surprisingly been discovered that these two components can provide a synergistic increase in the solubility of kinetin and/or zeatin that is greater than that which would be expected based on the solubility of the kinetin and/or the zeatin in the individual components. In one embodiment, the liposome forming agent in the formulations of the present invention is a polyoxyalkylene-n-glycerol dicarboxylate and the lipophilic skin penetration enhancing agent is a fatty acid. In certain embodiments, the formulations of the present invention may further comprise water and/or other pharmaceutical excipients known to those of skill in the art. Such pharmaceutical excipients include, for example, thickening and/or gelling agents, fatty ester based or waxy gelling agents, surfactants which may function as emulsifying agents, wetting agents, stabilizers, humectants, emollients, pH adjusting and stabilizing agents, preservatives, and anti-oxidants. In other embodiments, the formulation of the present invention comprises kinetin and/or zeatin, a liposome forming agent, a lipophilic skin penetration enhancing agent, water and, optionally, one or more pharmaceutically acceptable excipients.

These and other features, aspects, and embodiments of the present invention are described below in the section entitled "Detailed Description of the Invention" as well as in Examples 1-13 and the claims that follow.

DETAILED DESCRIPTION OF THE INVENTION

It has now been determined that there is a substantial need for a good solubilizing system for kinetin and/or zeatin that can be utilized in topical formulations such as creams, lotions, milks, foams, gels and the like. Such topical formulations are described herein. Additional benefits and advantages associated with the present invention are also further described herein.

In one aspect, it has been discovered that the solubilization of kinetin and/or zeatin is synergistically enhanced when formulated with a combination of a liposome forming agent and a lipophilic skin penetration enhancing agent. It has been further discovered that kinetin and/or zeatin does not precipitate from a formulation containing a liposome forming agent and a lipophilic skin penetration enhancing agent when combined with water.

Thus, in one aspect, this present invention provides a formulation containing kinetin and/or zeatin in which the kinetin and/or zeatin is contained as part of a liposome (or combined with a liposome forming agent) and wherein the kinetin and zeatin do not precipitate from the formulation upon mixture with water. This means that the kinetin and/or zeatin will not precipitate when they have been dissolved and then water is added to the solution or the solution is added to a water based formulation. The water may be included at a concentration of 50% or more without precipitation, preferably 75% or more, more preferably 85% or more, most preferably 90% or more without the precipitation of kinetin and/or zeatin from the formulation.

A liposome forming agent is a chemical compound that, when added to an aqueous liquid, forms liposomes. Preferred liposome forming agents are those that spontaneously form liposomes upon addition to an aqueous liquid, such as those disclosed in Keller, U.S. Pat. No. 6,610,322, the teachings of which are incorporated herein by reference.

A skin penetration enhancing agent is an agent that, when present in a formulation containing a cosmetic or pharmaceutical agent, increases the penetration of the cosmetic or pharmaceutical agent into or through the skin when the formulation is applied to the skin.

A lipophilic agent is a chemical compound that is miscible in a non-polar solvent such as hexane or toluene.

The term "hydrophobic" refers to the property of being repelled from water. Most, but not all, lipophilic agents are hydrophobic.

In another aspect, it has been further discovered that the solubility of kinetin is increased when combined in a formulation that includes a liposome forming agent, such as polyoxyalkylene-n-glycerol dicarboxylate component, and a lipophilic agent component, such as a lipophilic skin penetration enhancing agent component, such as a fatty acid component. In certain aspects, these two components can provide a synergistic increase in the solubility of kinetin that is greater than that which would be expected based on the solubility of kinetin in the individual components.

In another aspect, it has been further discovered that the solubility of zeatin is increased when combined in a formulation that includes a liposome forming agent, such as polyoxyalkylene-n-glycerol dicarboxylate component, and a lipophilic agent component, such as a lipophilic skin penetration enhancing agent component, such as a fatty acid component. These two components provide a synergistic increase in the solubility of zeatin that is greater than that which would be expected based on the solubility of zeatin in the individual components.

It has been discovered that the solubility of both kinetin and zeatin is increased when combined in a formulation that includes a liposome forming agent, such as polyoxyalkylene-n-glycerol dicarboxylate component, and a lipophilic agent component, such as a lipophilic skin penetration enhancing agent component, such as a fatty acid component. These two components provide a synergistic increase in the solubility of kinetin and zeatin that is greater than that which would be expected based on the solubility of kinetin and zeatin in the individual components.

In this application, polyoxyalkylene-n-glycerol dicarboxylate is used as a representative illustration of a liposome forming agent. The polyoxyalkylene-n-glycerol dicarboxylate component comprises two portions, a polyoxyalkylene portion and a glyceryl diester portion. The polyoxyalkylene portion of the polyoxyalkylene-n-glycerol dicarboxylate component may be, for example, a polyoxyethylene (PEG) or a polyoxypropylene (PPG). The "n" of polyoxyalkylene-n-glycerol can be between 6 to 100. Other suitable polyoxyalkylene portions include paraformaldehyde, polyethylene glycol, polypropylene glycol, and polytetramethylene glycol.

Examples of suitable glyceryl diesters for the glyceryl diester portion of the polyoxyalkylene-n-glycerol dicarboxylate component include, but are not limited to, glyceryl dilaurate, glyceryl diarachidate, glyceryl dibehenate, glyceryl dierucate, glyceryl dihydroxystearate, glyceryl diisopalmitate, glyceryl diisostearate, glyceryl dilinoleate, glyceryl dimyristate, glyceryl dioleate, glyceryl diricinoleate, glyceryl dipalmitate, glyceryl dipalmitoleate, glyceryl distearate, glyceryl palmitate lactate, glyceryl stearate citrate, glyceryl stearate lactate, and glyceryl stearate succinate.

GDM (PEG Glycerol dimyristate) is utilized in this application for illustration as a representative polyoxyalkylene-n-glycerol dicarboxylate, and GDM-12 (PEG-12) is utilized as a representative GDM. Likewise, GDO (PEG Glycerol dioleate) is utilized in this application for illustration as another representative polyoxyalkylene-n-glycerol dicarboxylate, and GDO-12 (PEG-12) is utilized as a representative GDO.

In this application, fatty acids as described below are utilized as a representative lipophilic skin penetration enhancing agent. Fatty acids are a preferred lipophilic skin penetration enhancing agent because, although fatty acids are hydrophobic, and the degree of hydrophobicity increases with increased carbon number, fatty acids will incorporate within the wall of a liposome due to the presence of a hydrophilic portion at one end and the hydrophobic portion at the other end. Lipophilic skin penetration enhancers other than fatty acids that may be used with the present application include, but are not limited to, dioctylcyclohexane, dodecanol, 2-octyldodecanol, 2-hexyldodecanol, oleyl alcohol, lauric acid, oleic acid, palmitic acid, dioctyl ether, isopropyl myristate, hexyl laurate, cetearyl isononanoate, capric acid, (C1- to C20-)alkyl caprates, (C1- to C20-)alkyl oleates, in particular decyl oleate, oleyl oleate, and (C1- to C20-)alkyl docosenoates).

The fatty acid component that is suitable for use in the present application is one or more fatty acids that are liquid at room temperature and that have a branched or unbranched chain of 6 to 30 carbons, typically 12 to 24 carbons. In one preferred embodiment, the fatty acid component is a branched fatty acid such as isostearic acid. Other preferred fatty acid components include, but are not limited to, oleic, linoleic, and linolenic acids, each of which has a carbon number of 18, and are unbranched and unsaturated. Yet another preferred fatty acid component is a multiplicity of fatty acids, such as a branched fatty acid and an unsaturated unbranched fatty acid. Fatty acids having carbon numbers from 6 to 30 are typically suitable for the fatty acid component, with the preferred fatty acids having carbon numbers from 12 to 24.

The relative concentrations of the polyoxyalkylene-n-glycerol dicarboxylate and the fatty acid components may be from 95:5 to 5:95% w/w or any ratio in between. For example, the ratio of the two components may be between 80:20 and 20:80, between 70:30 and 30:70, or between 60:40 and 40:60, such as about 50:50.

The pharmaceutical formulations containing kinetin and/or zeatin may further include pharmaceutically acceptable polymeric and/or non-polymeric excipients typically used in pharmaceutical formulations and known to those skilled in the art. Such excipients include, for example, thickening and/or gelling agents, fatty ester based or waxy gelling agents, surfactants which may function as emulsifying agents, wetting agents, stabilizers, humectants, emollients, pH adjusting and stabilizing agents, preservatives, and antioxidants.

The amount of kinetin in the formulations of the present invention may be from 0.001% to 1.0% w/w, such as between 0.01% to 0.5%, or between 0.05% to 0.4%, or between 0.1% to 0.3%. Examples of kinetin concentrations include 0.025%, 0.05%, 0.1%, and 0.2%.

The amount of zeatin in the formulations of the present invention may be from 0.001% to 1.0% w/w, such as between 0.01% to 0.5%, or between 0.05% to 0.4%, or between 0.1% to 0.3%. Examples of kinetin concentrations include 0.025%, 0.05%, 0.1%, and 0.2%.

The formulations containing kinetin and/or zeatin may be applied topically to the skin of an individual in order to repair damage to skin due to aging or sun exposure, and to reduce wrinkles. The formulations may be applied daily in an amount sufficient to cover the face or other areas of the body, such as those that are exposed to sun.

Studies were conducted that established the synergy in solubilizing kinetin and/or zeatin by the combination of a polyether glyceryl diester component and a fatty acid component and the maintenance of the solubility of kinetin and/or zeatin upon the addition of water. Solubilization of kinetin and zeatin was determined by HPLC.

EXAMPLES

Example 1—Kinetin Solubility

Kinetin was dissolved in 100% GDM-12 (PEG-12 Glycerol dimyristate) and determined to have a solubility of 0.16% w/w. Kinetin was dissolved in 100% isostearic acid and determined to have a solubility of 0.29% w/w. The calculated solubility of kinetin in a solvent system containing 50% GDM-12 and 50% isostearic acid, based on the determined independent solubility of kinetin in each of these two solvents, is 0.225 wt %. Kinetin was dissolved in 50% GDM-12 and 50% isostearic acid and determined to have a solubility of 0.42% w/w, an increase of 86% over the calculated solubility.

Example 2—Kinetin Solubility

Kinetin was dissolved in 100% GDO-12 (PEG-12 Glycerol dioleate) and determined to have a solubility of 0.09% w/w. Kinetin was dissolved in 100% isostearic acid and determined to have a solubility of 0.29% w/w. The calculated solubility of kinetin in a solvent system containing 50% GDO-12 and 50% isostearic acid, based on the determined independent solubility of kinetin in each of these two solvents, is 0.19 wt %. Kinetin was dissolved in 50% GDO-12 and 50% isostearic acid and determined to have a solubility of 0.39% w/w, an increase of 105% over the calculated solubility.

Example 3—Zeatin Solubility

Zeatin was dissolved in 100% GDM-12 (PEG-12 Glycerol dimyristate) and determined to have a solubility of 0.12% w/w. Zeatin was dissolved in 100% isostearic acid and determined to have a solubility of 0.30% w/w. The calculated solubility of zeatin in a solvent system containing 50% GDM-12 and 50% isostearic acid, based on the determined independent solubility of kinetin in each of these two solvents, is 0.21 wt %. Zeatin was dissolved in 50% GDM-12 and 50% isostearic acid and determined to have a solubility of 0.44% w/w, an increase of 109% over the calculated solubility.

Example 4—Zeatin Solubility

Zeatin was dissolved in 100% GDO-12 (PEG-12 Glycerol dioleate) and determined to have a solubility of 0.10% w/w. Zeatin was dissolved in 100% isostearic acid and determined to have a solubility of 0.30% w/w. The calculated solubility of zeatin in a solvent system containing 50% GDO-12 and 50% isostearic acid, based on the determined independent solubility of kinetin in each of these two solvents, is 0.20 wt %. Zeatin was dissolved in 50% GDO-12 and 50% isostearic acid and determined to have a solubility of 0.40% w/w, an increase of 100% over the calculated solubility.

Example 5—Kinetin Solubility when Both Kinetin and Zeatin are Dissolved

Both kinetin and zeatin were dissolved in 100% GDM-12 (PEG-12 Glycerol dimyristate) and the solubility of the kinetin was determined to be 0.16% w/w. Both kinetin and zeatin were dissolved in 100% isostearic acid, and the solubility of the kinetin was determined to be 0.22% w/w. The calculated solubility of kinetin in a solvent system containing 50% GDM-12 and 50% isostearic acid, based on the determined independent solubility of kinetin in each of these two solvents, when zeatin is combined with the kinetin, is 0.19 wt %. Both kinetin and zeatin were dissolved in 50% GDM-12 and 50% isostearic acid, and the kinetin was determined to have a solubility of 0.38% w/w, an increase of 100% over the calculated solubility.

Example 6—Kinetin Solubility when Both Kinetin and Zeatin are Dissolved

Both kinetin and zeatin were dissolved in 100% GDO-12 (PEG-12 Glycerol dioleate) and the solubility of the kinetin was determined to be 0.09% w/w. Both kinetin and zeatin were dissolved in 100% isostearic acid, and the solubility of the kinetin was determined to be 0.22% w/w. The calculated solubility of kinetin in a solvent system containing 50% GDO-12 and 50% isostearic acid, based on the determined independent solubility of kinetin in each of these two solvents, when zeatin is combined with the kinetin, is 0.155 wt %. Both kinetin and zeatin were dissolved in 50% GDO-12 and 50% isostearic acid, and the kinetin was determined to have a solubility of 0.36% w/w, an increase of 132% over the calculated solubility.

Example 7—Zeatin Solubility when Both Kinetin and Zeatin are Dissolved

Both kinetin and zeatin were dissolved in 100% GDM-12 (PEG-12 Glycerol dimyristate) and the solubility of the zeatin was determined to be 0.10% w/w. Both kinetin and zeatin were dissolved in 100% isostearic acid, and the solubility of the zeatin was determined to be 0.28% w/w. The calculated solubility of zeatin in a solvent system containing 50% GDM-12 and 50% isostearic acid, based on the determined independent solubility of zeatin in each of these two solvents, when a zeatin is combined with the kinetin, is 0.19 wt %. Both kinetin and zeatin were dissolved in 50% GDM-12 and 50% isostearic acid, and the zeatin was determined to have a solubility of 0.42% w/w, an increase of 121% over the calculated solubility.

Example 8—Facial Milk Containing Solubilized Kinetin Based on Example 1

| Ingredient | Amount (percent by weight) |
| --- | --- |
| Kinetin | 0.084 |
| GDM-12 | 10.000 |
| Isostearic Acid | 10.000 |
| Preservative | 0.250 |
| Purified Water | 79.666 |

The facial milk is made by combining the GDM-12 and isostearic acid in a beaker and mixing until homogeneous. Next, the kinetin is added and mixed at room temperature with a propeller mixer until fully homogenized. In a separate beaker containing the water, warmed to 40-45° C., add the preservative and mix with a propeller mixer until fully dissolved. Last, the kinetin solution is slowly added to the beaker containing water and preservative. Mixing is continued for 3-5 minutes. The kinetin does not precipitate from the formulation upon the combination with the water.

Example 9—Facial Milk Containing Solubilized Zeatin Based on Example 3

| Ingredient | Amount (percent by weight) |
| --- | --- |
| Zeatin | 0.088 |
| GDM-12 | 10.000 |
| Isostearic Acid | 10.000 |
| Preservative | 0.250 |
| Purified Water | 79.662 |

The facial milk is made by combining the GDM-12 and isostearic acid in a beaker and mixing until homogeneous. Next, the zeatin is added and mixed at room temperature with a propeller mixer until fully homogenized. In a separate beaker containing the water, warmed to 40-45° C., add the preservative and mix with a propeller mixer until fully dissolved. Last, the zeatin solution is slowly added to the beaker containing water and preservative. Mixing is continued for 3-5 minutes. The zeatin does not precipitate from the formulation upon the combination with the water.

Example 10—Throat Gel Containing Solubilized Kinetin and Zeatin Based on Examples 4 and 6

| Ingredient | Amount (percent by weight) |
| --- | --- |
| Kinetin | 0.108 |
| Zeatin | 0.120 |
| GDO-12 | 15.000 |
| Isostearic Acid | 15.000 |
| Preservative | 0.250 |
| Carbomer 980 (gelling agent) | 0.750 |

-continued

| Ingredient | Amount (percent by weight) |
|---|---|
| Trolamine (pH adjuster) | 0.350 |
| Purified Water | 68.422 |

The throat gel is made by combining the GDO-12 and isostearic acid in a beaker and mixing until uniform. Next, the kinetin and zeatin are added and the ingredients are mixed at room temperature with a propeller mixer until fully homogenized. In a separate beaker containing the water, warmed to 40-45° C., add the preservative and mix with a propeller mixer until fully dissolved. Next, slowly sprinkle the carbomer into the water-preservative solution while mixing, and continue mixing until homogeneous. Slowly add the kinetin-zeatin solution to the beaker containing water, preservative and carbomer. Continue mixing for 3-5 minutes. Finally, add the trolamine while continuing to mix for another 3-5 minutes. Complete the mixing by hand with a broad blade spatula to insure a homogeneous gel. The kinetin and zeatin do not precipitate from the formulation upon the combination with the water.

| Formulation | 11-A | 11-B | 11-C | 11-D | 11-E |
|---|---|---|---|---|---|
| Kinetin | 0.025 | 0.01 | 0.01 | 0.025 | 0.05 |
| Zeatin | 0.1 | 0.1 | 0.1 | 0.1 | 0.1 |
| Capric caprylic triglycerides | 2 | 2 | 4 | 4 | 3 |
| Isopropyl myristate | 3 | 3 | 2 | 1 | 2 |
| Polyoxyethylene (21) Stearyl ether | 2 | 3 | 1 | 2 | 3 |
| Polyoxyethylene (2) Stearyl ether | 1 | 1.5 | 0.75 | 1 | 1.5 |
| Cetostearyl alcohol | 2.5 | 2.5 | 2.5 | 2.5 | 2.5 |
| Butylated hydroxytoluene | 0.1 | 0.1 | 0.1 | 0.1 | 0.1 |
| Phenoxyethanol | 0.9 | 0.9 | 0.9 | 0.9 | 0.9 |
| Ethylhexyl glycerin | 0.1 | 0.1 | 0.1 | 0.1 | 0.1 |
| GDM-12 | 3.6 | 2.25 | | 3.6 | 3.6 |
| GDS-12 | | | 2.25 | | |
| Isostearic acid | | | 0.25 | | 0.4 |
| Oleic acid | | | | 0.4 | |
| Water | | | qs 100 | | |

Example 11—Formulations Containing Kinetin and Zeatin

Formulations 11-A, 11-B, 11-C, 11-D, and 11-E are made with the constituents shown in the above table, as follows. (1) Combine the GDO-12 or GDS-12 and isostearic acid or oleic acid in a first beaker and mix until uniform. (2) The kinetin, zeatin, and butylated hydroxytoluene are added and the ingredients are mixed at room temperature with a propeller mixer until fully homogenized. (3) In a second beaker add the following ingredients and mix while heating to about 75° C.: capric caprylic triglycerides, isopropyl myristate, polyoxyethylene (21) stearyl ether, polyoxyethylene (2) stearyl ether, and cetostearyl alcohol. 4. In a separate third beaker containing the water, warmed to 75° C., add the phenoxyethanol and ethylhexyl glycerin and mix with a propeller mixer until dissolved. (5) Add the hot contents of the second beaker slowly to the hot water mixture in the third beaker while mixing. Mix while cooling to between 30 and 40° C. (6) Last, slowly add the kinetin-zeatin solution to the beaker containing water, preservative and carbomer. Continue mixing for 3-5 minutes. Allow to cool to room temperature while continuing to mix. The kinetin and zeatin do not precipitate from the formulations when combined with the water.

Example 12—Comparison with Prior Art Formulations

Kinetin was combined and mixed in separate beakers containing GDM-12, Transcutol, and Isostearic Acid, and the concentration of dissolved kinetin in each beaker was determined by HPLC. Kinetin was then combined and mixed in separate beakers containing GDM-12 and Transcutol (1:1) and containing GDM-12 and Isostearic acid. The amount of dissolved kinetin was determined by HPLC and the results are shown in Table Example 12.

TABLE EXAMPLE 12

| Solvent | Kinetin % w/w Experimental | Kinetin % w/w Calculated | Synergistic Increase in Solubility % |
|---|---|---|---|
| GDM-12 | .164 | | |
| Transcutol | .397 | | |
| GDM-12 + Transcutol (1:1) | .287 | .281 | 0% |
| Isostearic Acid | .299 | | |
| GDM-12 + Isostrearic Acid | .422 | .229 | 84% |

As shown in Table Example 12, combining kinetin with a liposome forming agent, GDM-12, plus a lipophilic skin penetration enhancing agent, isostearic acid, produced an 84% increase in solubility above what is calculated based on the solubility of kinetin in GDM-12 and isostearic acid alone. In contrast, combining kinetin with GDM-12 plus a hydrophilic skin penetrating agent, Transcutol, does not provide a synergistic increase in solubility of the kinetin.

Example 13—Comparison with Prior Art Formulations

Zeatin was combined and mixed in separate beakers containing GDM-12, Transcutol, and Isostearic Acid, and the concentration of dissolved zeatin in each beaker was determined by HPLC. Zeatin was then combined and mixed in separate beakers containing GDM-12 and Transcutol (1:1) and containing GDM-12 and Isostearic acid. The amount of dissolved zeatin was determined by HPLC and the results are shown in Table Example 13.

TABLE EXAMPLE 13

| Solvent | Zeatin % w/w Experimental | Zeatin % w/w Calculated | Synergistic Increase in Solubility % |
|---|---|---|---|
| GDM-12 | .119 | | |
| Transcutol | .570 | | |
| GDM-12 + Transcutol (1:1) | .365 | .345 | 0% |
| Isostearic Acid | .299 | | |
| GDM-12 + Isostrearic Acid | .440 | .229 | 92% |

As shown in Table Example 13, combining zeatin with a liposome forming agent, GDM-12, plus a lipophilic skin penetration enhancing agent, isostearic acid, produced a 92% increase in solubility above what is calculated based on the solubility of zeatin in GDM-12 and isostearic acid alone. In contrast, combining zeatin with GDM-12 plus a hydrophilic skin penetrating agent, Transcutol, does not provide a synergistic increase in solubility of the zeatin.

Although the above description specifically pertains to increasing the solubility of kinetin and zeatin, and maintaining the solubilization of kinetin and zeatin in a liposome-based formulation upon the combination with water, this invention is not limited to these two biologically active ingredients, but rather has application to other compounds within the nucleic acids and purine based molecules. Thus, one skilled in the art would understand from this description that the solubility of other purine based molecules, such as adenine, guanine, hypoxanthine, xanthine, theobromine, caffeine uric acid, and isoguanine, may also be increased by the methods disclosed in this application.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A formulation comprising kinetin and/or zeatin in which the kinetin and/or zeatin is contained as part of a liposome and wherein the kinetin and zeatin do not precipitate from the formulation in the presence of water, wherein the formulation comprises a polyoxyalkylene-n-glycerol dicarboxylate component and a fatty acid component.

2. The formulation of claim 1, wherein the amounts of the polyoxyalkylene-n-glycerol dicarboxylate component and the fatty acid component are sufficient to provide a synergistic increase in the solubility of the kinetin and/or the zeatin in the formulation.

3. The formulation of claim 1, wherein the polyoxyalkylene of the polyoxyalkylene-n-glycerol dicarboxylate component is selected from the group consisting of paraformaldehyde, polyethylene glycol, polypropylene glycol, and polytetramethylene glycol.

4. The formulation of claim 1, wherein the glyceryl dicarboxylate of the polyoxyalkylene-n-glycerol dicarboxylate component is selected from the group consisting of glyceryl dilaurate, glyceryl diarachidate, glyceryl dibehenate, glyceryl dierucate, glyceryl dihydroxystearate, glyceryl diisopalmitate, glyceryl diisostearate, glyceryl dilinoleate, glyceryl dimyristate, glyceryl dioleate, glyceryl diricinoleate, glyceryl dipalmitate, glyceryl dipalmitoleate, glyceryl distearate, glyceryl palmitate lactate, glyceryl stearate citrate, glyceryl stearate lactate, and glyceryl stearate succinate.

5. The formulation of claim 1, wherein the fatty acid component comprises one or more fatty acids that are liquid at room temperature or that have a branched or unbranched chain of 12 to 20 carbons.

6. The formulation of claim 5, wherein the fatty acid component comprises a mixture of fatty acids.

7. The formulation of claim 6, wherein the fatty acid component is a mixture of branched and straight-chain unsaturated C18 fatty acids.

8. The formulation of claim 7, wherein the fatty acid component is a mixture of fatty acids having between 12 and 20 carbons.

9. The formulation of claim 7, wherein the fatty acid component is a mixture of fatty acids comprising branched and straight chain fatty acids.

10. The formulation of claim 7, wherein the fatty acid component is a mixture of fatty acids comprising saturated and unsaturated fatty acids.

11. The formulation of claim 1, wherein the polyoxyalkylene-n-glycerol dicarboxylate component is PEG-12 Glycerol dimyristate or PEG-12 Glycerol dioleate.

12. The formulation of claim 1, wherein the fatty acid component is isostearic acid.

13. The formulation of claim 1, wherein the polyoxyalkylene-n-glycerol dicarboxylate component is PEG-12 Glycerol dimyristate or PEG-12 Glycerol dioleate, and the fatty acid component is isostearic acid.

14. The formulation of claim 1, wherein the formulation comprises only kinetin.

15. The formulation of claim 1, wherein the formulation comprises only zeatin.

16. The formulation of claim 1, wherein the formulation comprises both kinetin and zeatin.

17. A formulation comprising kinetin and/or zeatin in which the kinetin and/or zeatin is contained as part of a liposome, wherein the formulation includes a polyoxyalkylene-n-glycerol dicarboxylate component and a fatty acid component, wherein the amounts of the polyoxyalkylene-n-glycerol dicarboxylate and the fatty acid are sufficient to provide a synergistic increase in the solubility of the kinetin and/or the zeatin in the formulation.

18. A method of delivering kinetin and/or zeatin to a subject in need thereof, said method comprising administering to the skin of the subject a formulation of claim 1.

* * * * *